(12) United States Patent
Shimada et al.

(10) Patent No.: US 6,767,343 B2
(45) Date of Patent: Jul. 27, 2004

(54) DISPOSABLE PULL-ON DIAPER

(75) Inventors: Takaaki Shimada, Kagawa-ken (JP); Kenji Nakamura, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 0 days.

(21) Appl. No.: 09/943,172

(22) Filed: Aug. 30, 2001

(65) Prior Publication Data

US 2002/0029028 A1 Mar. 7, 2002

(30) Foreign Application Priority Data

Sep. 1, 2000 (JP) ........................................ 2000-266104

(51) Int. Cl.[7] .............................................. A61F 13/15
(52) U.S. Cl. ............................. 604/385.25; 604/385.28
(58) Field of Search ........................ 604/385.24–385.29, 604/385.01

(56) References Cited

U.S. PATENT DOCUMENTS

| | | | |
|---|---|---|---|
| 4,795,454 A | | 1/1989 | Dragoo |
| 5,188,627 A | * | 2/1993 | Igaue et al. ................. 604/358 |
| 5,342,342 A | * | 8/1994 | Kitaoka .................... 604/385.2 |
| 5,662,637 A | * | 9/1997 | Kitaoka et al. ......... 604/385.28 |
| 5,836,931 A | * | 11/1998 | Toyoda et al. .............. 604/358 |
| 6,120,486 A | * | 9/2000 | Toyoda et al. ......... 604/385.29 |
| 6,306,122 B1 | * | 10/2001 | Narawa et al. ........ 604/385.01 |
| 6,369,291 B1 | * | 4/2002 | Uchimoto et al. .......... 604/367 |

FOREIGN PATENT DOCUMENTS

| | | |
|---|---|---|
| EP | 0 516 877 A1 | 12/1992 |
| JP | 9-24063 | 1/1997 |
| JP | 09024063 | 1/1997 |

* cited by examiner

*Primary Examiner*—John J. Calvert
*Assistant Examiner*—C. Lynne Anderson
(74) *Attorney, Agent, or Firm*—Butzel Long

(57) ABSTRACT

A disposable pull-on diaper that includes elastic members attached under tension to peripheral edge portions of leg-openings and a pair of leak-barrier cuffs provided in the vicinity of transversely opposite side edges of a core. The elastic members associated with the leg-openings include first elastic members extending along front peripheral edge portions of the leg-openings and second elastic members extending along rear peripheral edge portions of the leg-openings and, in a crotch region, the free side edge portions of the leak-barrier cuffs extend inward beyond the side edges of said core and are folded back along substantially middle folding zones thereof outward beyond the side edges of the core and wherein the free side edge portions are bonded, in the vicinity of the folding zones, to the outer surface of the topsheet in the upper zone of the core.

4 Claims, 4 Drawing Sheets

DISPOSABLE PULL-ON DIAPER

BACKGROUND OF THE INVENTION

This invention relates to a disposable pull-on diaper adapted to absorb and hold excretion discharged thereon.

Japanese Patent Application Publication No. 1997-24063A describes a pants-type disposable diaper basically comprising a liquid-pervious topsheet, a liquid-impervious backsheet and a liquid-absorbent core disposed between the top- and backsheets, configuring front and rear waist regions opposed to each other and a crotch region extending between these two waist regions so that the front and rear waist regions may be connected to each other to a waist-opening and a pair of leg-openings, wherein elastic members being stretchable in a leg-surrounding direction are attached under tension to peripheral edge portions of the leg-openings, the diaper further comprising a pair of substantially liquid-impervious leak-barrier cuffs (flaps) extending in the leg-surrounding direction in the vicinity of transversely opposite side edges of the core.

In the case of this diaper of prior art, each of the leak-barrier cuffs (flaps) comprising inner and outer sections has a fixed side edge portion, a free side edge portion normally biased to rise on the topsheet and fixed longitudinally opposite end portions collapsed inwardly of the diaper. The respective fixed side edge portions are bonded to the topsheet in the vicinity of transversely opposite side edges of the core and the respective fixed end portions are bonded to the topsheet in the front and rear waist regions. The elastic members being stretchable in the leg-surrounding direction are attached under tension to the respective free side edge portions. In the crotch region, the free side edge portions defining the outer cuffs (flaps) extend inwardly of the core and these free side edge portions are folded back along substantially middle zones thereof outwardly of the core.

The diaper disclosed in the Publication is adapted to be worn in the manner that a wearer inserts his or her legs into the respective leg-openings and then the diaper is pulled up to the wearer's waist. In the case of this diaper, the elastic members associated with the leg-openings extend along the entire peripheral edge portions of the respective leg-openings and the middle zones of the respective outer cuff (flap) sections along which the free side edge portions are folded back outwardly of the core are not bonded to the diaper and the free side edge portions of the respective outer cuff (flap) sections rising in the crotch region define relatively high barriers. With a disadvantageous consequence, contraction of the elastic members associated with the leg-openings as well as rising of the free side edge portions of the outer cuff (flap) sections reduce the respective leg-openings. As a result, the free side edge portions of the respective outer cuff (flap) sections extending in the crotch region may obstruct the wearer's legs against being smoothly inserted into the respective leg-openings and make wearing time-consuming operation.

SUMMARY OF THE INVENTION

It is an object of this invention to provide a disposable pull-on diaper adapted to be smoothly worn without an anxiety that the free side edge portions of the leak-barrier cuffs might obstruct the wearer's legs against easily being inserted into the leg-openings.

According to this invention, there is provided a disposable pull-on diaper basically comprising a liquid-pervious topsheet, a liquid-impervious backsheet and a liquid-absorbent core disposed between the top- and backsheets, configuring front and rear waist regions opposed to each other and a crotch region extending between these two waist regions so that the front and rear waist regions may be connected to each other to form a waist-opening and a pair of leg-openings, wherein elastic members being stretchable in a leg-surrounding direction are attached under tension to peripheral edge portions of the leg-openings, the diaper further comprising a pair of substantially liquid-impervious leak-barrier cuffs extending in the leg-surrounding direction in the vicinity of transversely opposite side edges of the core.

According to this invention the elastic members associated with the leg-openings comprise first elastic members extending in the leg-surrounding direction along a front peripheral edge portion of the leg-opening on the side of the front waist region and second elastic members extending in the leg-surrounding direction along a rear peripheral edge portion of the leg-opening on the side of the rear waist region wherein none of the elastic members associated with the leg-openings are present along an intermediate peripheral edge portions extending between the front and rear peripheral edge portions of the leg-opening, the leak-barrier cuffs respectively have fixed side edge portions extending in the leg-surrounding direction in the vicinity of the respective side edge portions of the core, free side edge portions being contiguous to the fixed side edge portions and normally biased to rise on the topsheet and fixed longitudinally opposite end portions collapsed inwardly of the diaper and placed upon the topsheet in the front and rear waist region and, in the crotch region, the free side edge portions extend inward beyond the side edges of the core and are folded back along substantially middle folding lines thereof outward beyond the side edges of the core wherein the free side edge portions are bonded, in the vicinity of the middle folding lines, to the outer surface of the topsheet in the upper zone of the core.

According to one embodiment of this invention, the first elastic members present a stretch stress higher than that of the second elastic members.

DETAILED DESCRIPTION OF THE PREFERRED EMBODIMENTS

Details of the disposable pull-on wearing article according to this invention will be more fully understood from the description of a disposable pull-on diaper as a typical embodiment given hereunder with reference to the accompanying drawings.

Figure 1:
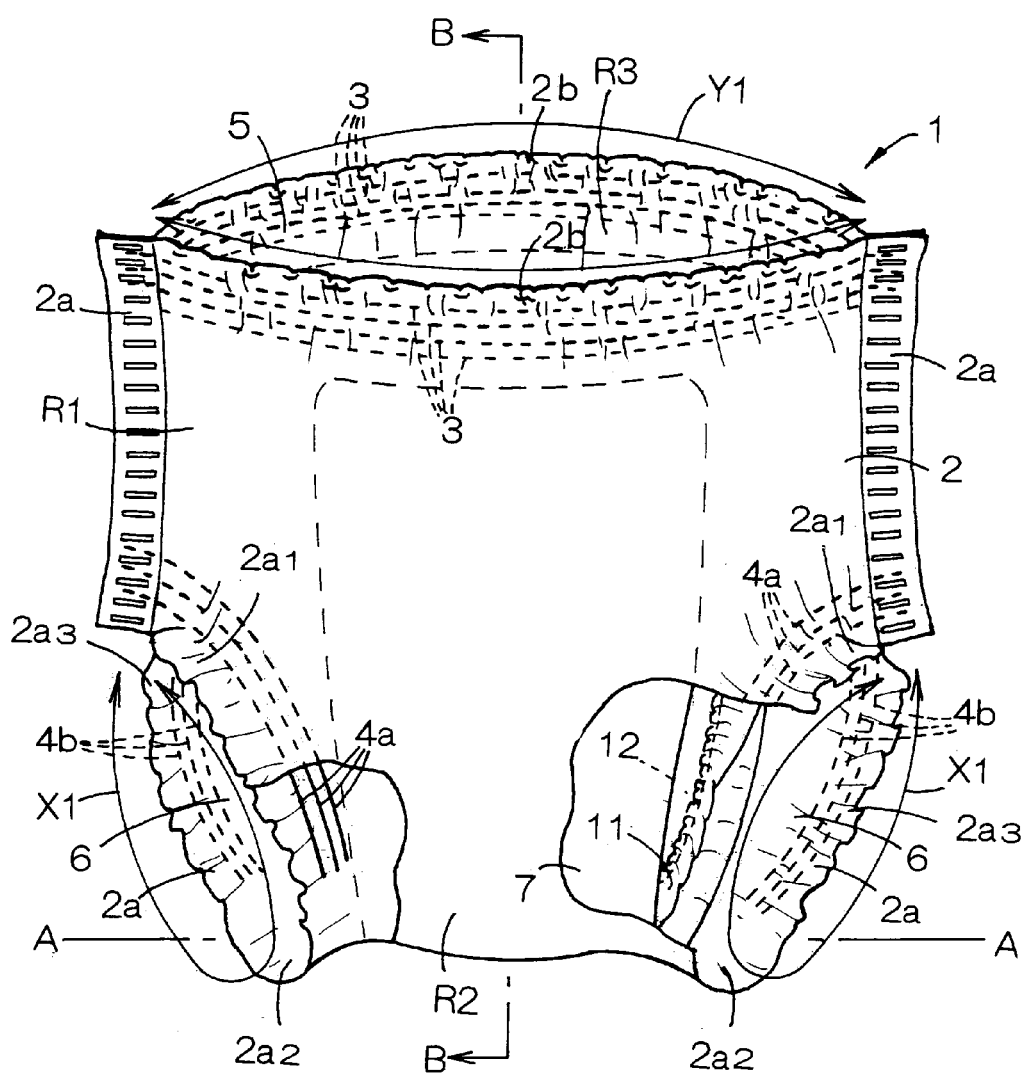
FIG. 1 is a perspective view showing an embodiment of a disposable pull-on diaper according to this invention as partially broken away.
Figure 2:
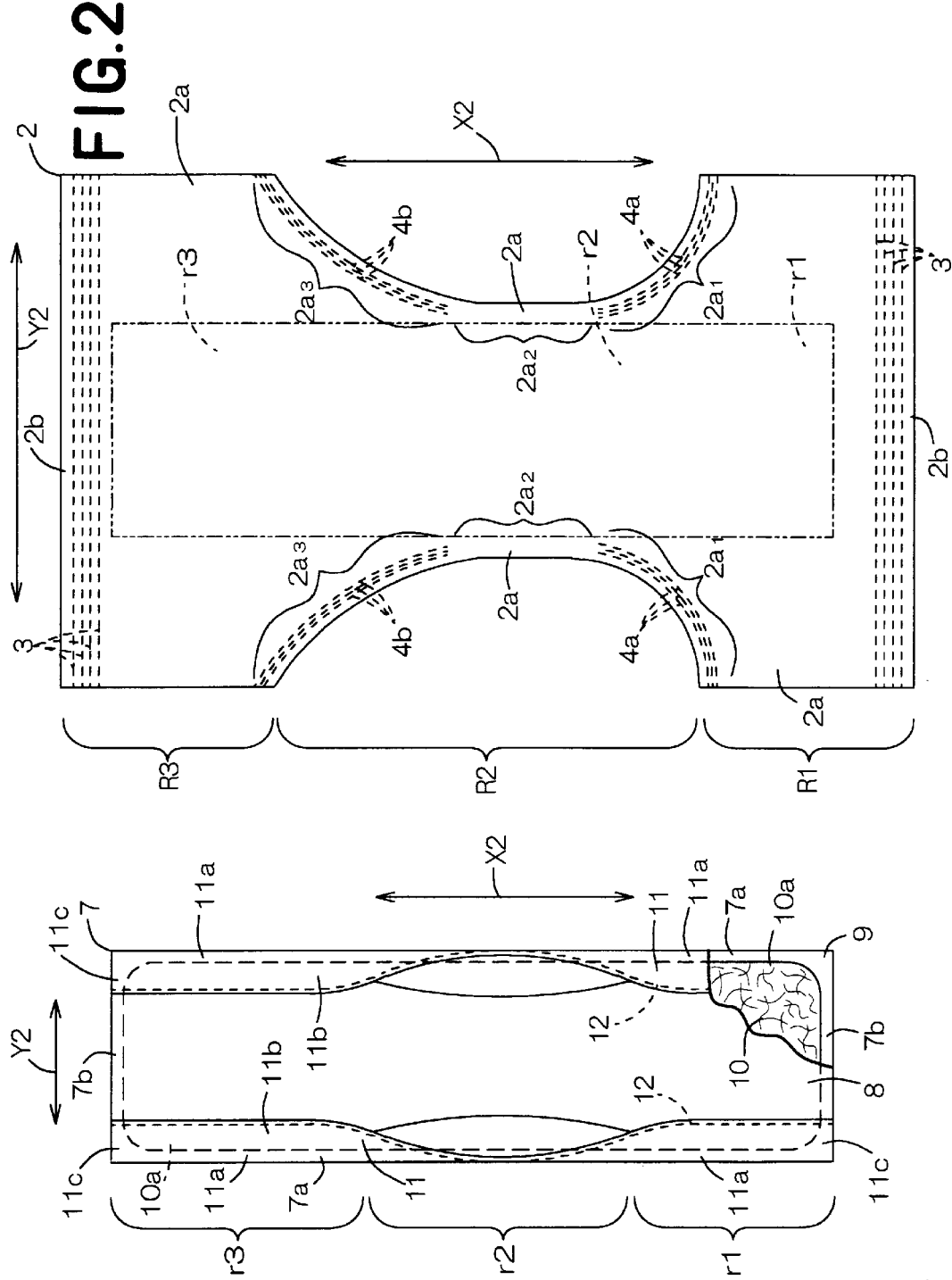
FIG. 2 is a plan view separately showing the pants and the pad constituting the diaper.

FIG. 1 is a perspective view showing an embodiment of a disposable pull-on diaper 1 according to this invention as partially broken away and FIG. 2 is a plan view separately showing the pants 2 and the pad 7 constituting the diaper 1 as front and rear waist regions R1, R3 have been disconnected from each other and the diaper 1 has been developed in its longitudinal direction. Referring to FIG. 1, a leg-surrounding direction is indicated by an arrow X1 and a waist-surrounding direction is indicated by an arrow Y1. Referring to FIG. 2, a longitudinal direction is indicated by an arrow X2 and a transverse direction is indicated by an arrow Y2. The herein used expression "inner surfaces" of the pants 2 as well as the top- and backsheets should be understood to be the surfaces thereof facing a core and the expression "outer surfaces" thereof should be understood to be the surfaces thereof being remote from the core.

The diaper 1 comprises the pants 2 and a liquid-absorbent pad 7 attached to the inner surface of the pants 2. The pants 2 comprise two layers of a nonwoven fabric placed one upon another so that surfaces thereof opposed to each other are intermittently bonded together. The pad 7 comprises a liquid-pervious topsheet 8, a liquid-impervious backsheet 9, a liquid-absorbent core 10 and pair of substantially liquid-impervious leak-barrier cuffs 11.

The pants 2 are composed of front and rear waist regions R1, R3 opposed to each other and a crotch region R2 extending between these two waist regions R1, R3. As will be apparent from FIG. 2, the pants 2 are contoured by transversely opposite side edge portions 2a extending in parallel to each other in the longitudinal direction and curving inward in the transverse direction of the pants 2 in the crotch region R2 so as to describe circular arcs and longitudinally opposite end portions 2b extending in parallel to each other in the transverse direction. In the pants 2, the front and rear waist regions R1, R3 are bonded intermittently along the side edge portions 2a of the pants 2 so as to define a waist-opening 5 and a pair of leg-openings 6. The longitudinally opposite end portions 2b define a peripheral edge portion of the waist-opening 5 and the transversely opposite side edge portions 2a in the crotch region R2 define peripheral edge portions of the respective leg-openings 6.

The waist-opening 5 is provided along its peripheral edge portion 2b with a plurality of elastic members 3 being stretchable in the waist-surrounding direction and attached under tension thereto. These elastic members 3 associated with the waist-opening are covered with a part of the peripheral edge portion 2b of the waist-opening 5 which is folded back onto the inner surface of the pants 2.

Each of the leg-openings 6 is provided along its peripheral edge portion 2a with a plurality of elastic members being stretchable in the leg-surrounding direction and attached under tension thereto between two layers of the nonwoven fabric. These elastic members associated with each of the leg-openings comprise first elastic members 4a extending along a front peripheral edge portion $2a_1$ of the leg-opening 6 on the side of the front waist region R1 and second elastic members 4b extending along a rear peripheral edge portion $2a_3$ of the leg-opening 6 on the side of the rear waist region R3. None of the elastic members associated with each of the leg-openings are present along an intermediate peripheral edge portions $2a_2$ extending between the front and rear peripheral edge portions $2a_1$, $2a_3$ of the leg-opening 6.

In the pants 2, a stretch stress of the first elastic member 4a is adjusted to be higher than that of the second elastic members 4b so that the front peripheral edge portions $2a_1$ liable to be affected by movement of the wearer's legs can be tightly placed against the wearer's thighs and thereby excretion leak from the front peripheral edge portions $2a_1$ can be reliably prevented.

The pad 7 is substantially rectangular and has a front zone r1, a rear zone r3 and an intermediate zone r2 extending between the front and rear zones r1, r3. As shown in FIG. 2, the pad 7 has transversely opposite side edge portions 7a extending in parallel in the longitudinal direction and longitudinally opposite end portions 7b extending in parallel in the transverse direction. As indicated by chain lines, the front zone r1 lies in the front waist region R1 of the pants 2, the intermediate zone r2 lies in the crotch region R2 of the pants 2 and the rear zone r3 lies in the rear waist region R3. In the pad 7, the outer surface of the backsheet 9 is bonded to the inner surface of the pants 2.

The core 10 is disposed between the top- and backsheets 8, 9 and entirely covered with tissue paper 13 (See FIG. 3) and bonded to the inner surface of at least one of the top- and backsheets 8, 9 with the tissue paper 13 therebetween.

The cuffs 11 respectively have fixed side edge portions 11a extending in the leg-surrounding direction in the vicinity of the respective side edge portions 10a of the core 10, free side edge portions 11b being contiguous to the fixed side edge portions 11a and normally biased to rise on the topsheet and fixed longitudinally opposite end portions 11c collapsed inward in the transverse direction of the pad 7. The free side edge portions 11b are provided with elastic members 12 being stretchable in the leg-surrounding direction and bonded under tension thereto. These elastic members 12 are covered with a part of the free side edge portions 11b. The fixed end portions 11c are bonded to the outer surface of the topsheet 8 in the front and rear zones r1, r3 of the pad 7.

In the diaper 1, the peripheral edge portion 2b of the waist-opening 5, the peripheral edge portions 2a of the leg-openings 6 and the free side edge portions 11b of the cuffs 11 are formed with a plurality of gathers as the elastic members 3, 4a, 4b, 12 contract. In the diaper 1, the pad 7 curves, in the longitudinal direction, with the topsheet 8 inside and the free side edge portions 11b of the respective cuffs 11 rise on the topsheet 8 as the elastic members 12 contract.

Figure 3:
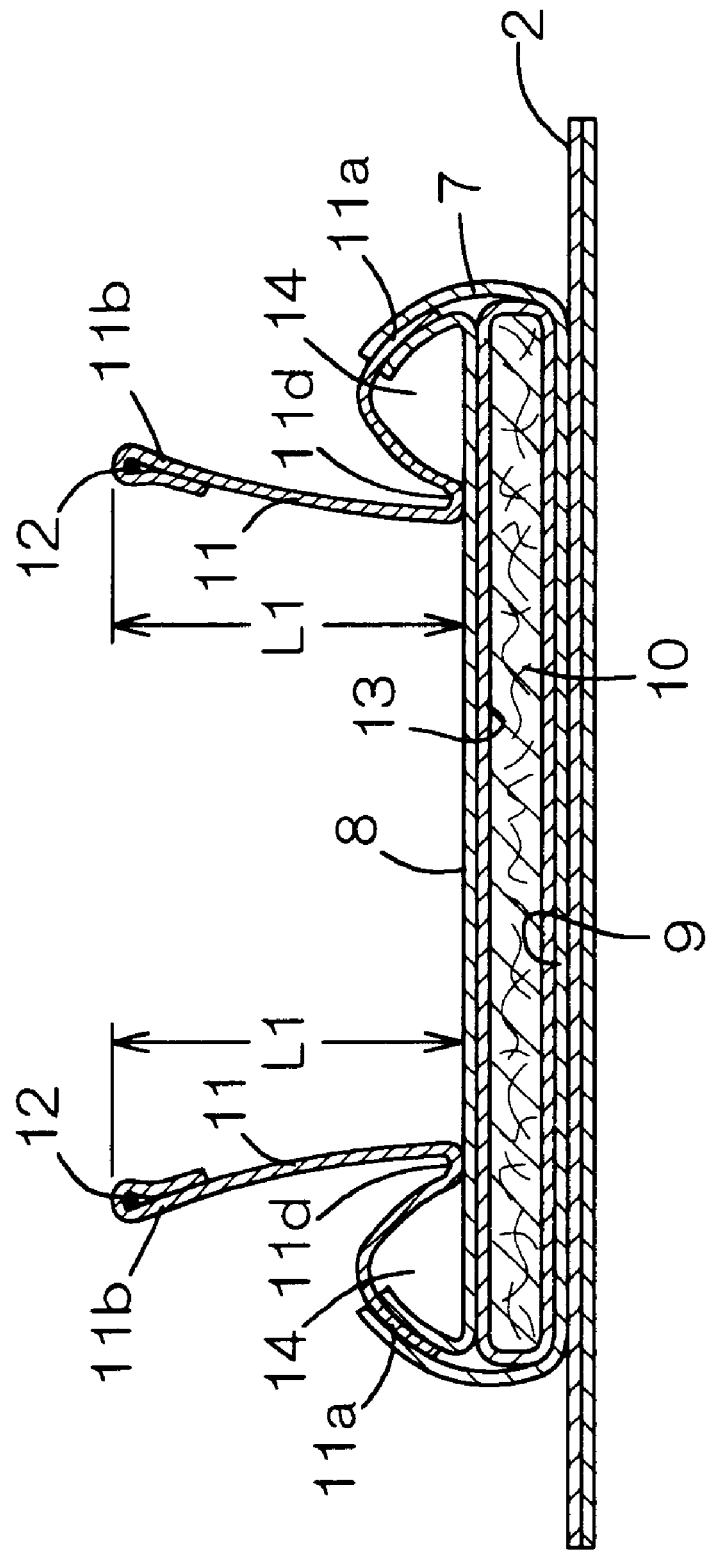
FIG. 3 is a sectional view taken along a line A—A in FIG. 1.
Figure 4:
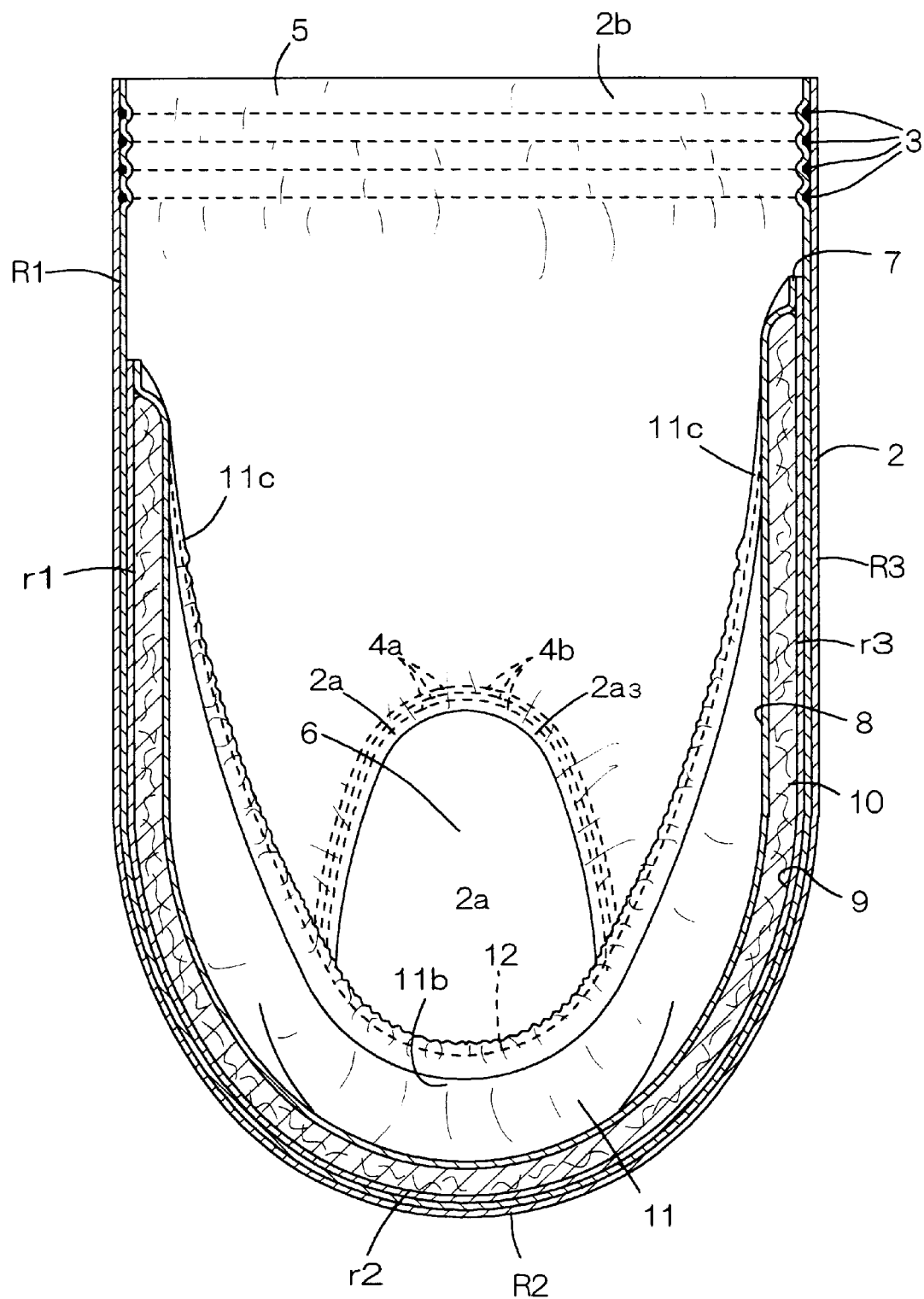
FIG. 4 is a sectional view taken along a line B—B in FIG. 1.

FIG. 3 is a sectional view taken along a line A—A in FIG. 1 and FIG. 4 is a sectional view taken along a line B—B in FIG. 1. The fixed side edge portions 11a of the respective cuffs 11 are disposed between the top- and backsheets 8, 9 and bonded to respective inner surfaces of these sheets 8, 9. In the intermediate zone r2 of the pad 7, the free side edge portions 11b extend inward in the transverse direction beyond the side edges 10a of the core 10 and the free side edge portions 11b are folded back along substantially middle folding lines thereof outward beyond the side edges 10a of the core 10. In the vicinity of the middle folding lines 11d, the free side edge portions 11b are bonded to the outer surface of the topsheet 8 in the upper zone of the core 10.

Of the respective free side edge portions 11b, a dimension L1 as measured from the folding lines 11d to the upper ends is preferably in a range of 10~50 mm. If the dimension L1 is less than 10 mm, the free side edge portions 11b could not rise to a height sufficient to fulfill their desired leak-barrier function and excretion leak would readily occur from the crotch region R2. If the dimension L1 exceeds 50 mm, on the contrary, the free side edge portions 11b of the cuffs would often obstruct the wearer's legs from being smoothly inserted into the respective leg-openings 6 when the diaper 1 is put on the wearer's body.

In the pad 7, the rising free side edge portions 11b of the respective cuffs 11 for barriers of an appropriate height to prevent excretion leak from the side edges 7a of the pad 7. In the pad 7, cavities 14 are defined between portions of respective cuffs 11 extending from the folds 11d to the fixed side edge portions 11a, on one hand, and the topsheet 8, on the other hand. Excretion can be absorbed within these cavities 14 also and, in this way, the entire upper surface of the pad 7 can be effectively utilized.

In the diaper 1 according to this embodiment, none of the elastic members associated with the leg-opening 6 are present along the intermediate peripheral edge portions 2a of the leg-opening 6, i.e., the peripheral edge portion 2a of the leg-opening 6 can only partially contract. In addition to this feature, the dimension L1 by which the free side edge portions 11b of the cuffs 11 rise is limited to the range, so it can be avoided that the free side edge portions 11b might form relatively high barriers in the crotch region R2. Before the diaper 1 is worn, therefore, it is not apprehended that the leg-openings 6 might be significantly reduced even when the first and second elastic members 4a, 4b contract and consequently the free side edge portions 11b of the cuffs 11 rise. This means that the free side edge portions 11b of the cuffs 11 extending in the crotch region R2 do not obstruct the wearer's legs from being smoothly inserted into the respective leg-openings 6 when the diaper 1 is put on the wearer's body.

The pants 2 are preferably formed with a hydrophobic nonwoven fabric. The pants 2 may be also formed with a composite sheet consisting of a stretchable nonwoven fabric, a hydrophobic nonwoven fabric and a plastic film laminated one upon another.

The top sheet may be formed from a liquid-pervious sheet such as a nonwoven fabric or a porous plastic film, more preferably from a liquid-pervious and a hydrophilic sheet. The backsheet 9 may be formed from a hydrophobic nonwoven fabric, a liquid-impervious plastic film or a laminated sheet consisting of a hydrophobic nonwoven fabric and a plastic film, more preferably from a breathable and a liquid-impervious sheet. The cuffs 11 may be formed from a hydrophobic nonwoven fabric. It is also possible to form the backsheet 9 and the cuffs 11 from a composite nonwoven fabric comprising highly water-resistant melt blown nonwoven fabric and two layers of spun bond nonwoven fabric having high strength and flexibility and sandwiching therebetween the melt blown nonwoven fabric.

The nonwoven fabric used for this invention may be of various types such as spun lace-, needle punch-, melt blown-, thermal bond-, spun bond-, chemical bond- and air through-types. The component fiber of the nonwoven fabric may be selected from a group including polyolefine-, polyester- and polyamide-based fibers and core-sheath- or side-by-side-type polyethylene/polypropylene or polyester conjugated fibers.

The core 10 comprises a mixture of fluff pulp, high absorption polymer grains and thermoplastic synthetic resin fiber compressed to a desired thickness. The polymer grains may be selected from a group including graft polymer of starch-based, cellulose-based and synthetic polymers.

Bonding the nonwoven fabric, bonding of the top- and backsheets 8, 9 to each other or bonding of the cuffs 11 and the core 10 to the top- and backsheets 8, 9, and attaching of the elastic members 12 to the cuffs 11 may be carried out using suitable adhesive such as hot melt adhesive or using suitable welding technique such as heat sealing or supersonic sealing technique.

The disposable diaper according to this invention has a unique arrangement such that the elastic members associated with the leg-openings comprise first elastic members extending along the front peripheral edge portions of the respective leg-openings and the second elastic members extending along the rear peripheral edge portions of the respective leg-openings and the elastic members are absent along the intermediate peripheral edge portions of the respective leg-openings. Such unique arrangement prevents the entire peripheral edge portions of the respective leg-openings from contracting under the effect of the elastic members associated with the leg-openings. Another important feature of this diaper lies in that the free side edge portions of the respective cuffs are bonded in the vicinity of the folded zones to the topsheet in the upper part of the core so that the rising free side edge portions of the respective cuffs may not form undesirably high barriers in the crotch region. In this way, the diaper according to this invention avoids the inconvenience that the leg-openings might be made extremely narrow as the diaper of prior art has been the case. Thus, there is no anxiety that the free side edge portions of the cuffs extending in the crotch region might obstruct smooth insertion of the wearer's legs into the respective leg-openings to wear the diaper.

What is claimed is:

1. A disposable pull-on diaper comprising:

a liquid-pervious top sheet;

a liquid-impervious backsheet;

a liquid-absorbent core disposed between said liquid-pervious topsheet and said liquid-impervious backsheet;

a front waist region;

a rear waist region opposed to said front waist region;

a waist-opening;

a pair of leg-openings having peripheral edge portions;

elastic members attached under tension to said peripheral edge portions of said leg-openings, said elastic members being stretchable in a leg-surrounding direction; and a pair of substantially liquid-impervious leak-barrier cuffs extending in said leg-surrounding direction in a vicinity of transversely opposite side edges of said liquid-absorbent core, said elastic members comprising:

first elastic members extending in said leg-surrounding direction along a front peripheral edge portion of said leg-openings on a side of said front waist region; and second elastic members extending in said leg-surrounding direction along a rear peripheral edge portion of the leg-openings on a side of the rear waist region, said first elastic members and said second elastic members being spaced apart in said leg-surrounding direction at an intermediate peripheral edge portion extending between said front and rear peripheral edge portions of said leg-openings, said leak-barrier cuffs having:

fixed side edge portions extending in said leg-surrounding direction in a vicinity of side edge portions of said liquid-absorbent core;

free side edge portions being contiguous to said fixed side edge portions and normally biased to rise on said liquid-pervious topsheet; and fixed longitudinally opposite end portions collapsed inwardly of said diaper and placed upon said liquid-pervious topsheet in said front and rear waist regions, said free side edge portions of said leak-barrier cuffs extending inward beyond the side edges of said liquid-absorbent core in said crotch region and being folded back along substantially middle folding lines thereof outward beyond the side edges of said liquid-absorbent core to define hollow cavities that extend within said crotch region, said free side edge portions of said leak-barrier cuffs are bonded, in the vicinity of said middle folding lines, to an outer surface of said liquid-pervious topsheet in an upper zone of the liquid-absorbent core.

2. The diaper according to claim 1, wherein said first elastic members have a stretch stress higher than a stretch stress of said second elastic members.

3. A disposable pull-on diaper comprising:

a liquid-pervious topsheet;

a liquid-impervious backsheet;

a liquid-absorbent core disposed between said liquid-pervious topsheet and said liquid-impervious backsheet;

a front waist region;

a rear waist region opposed to said front waist region;

a waist-opening;

a pair of leg-openings having peripheral edge portions;

elastic members attached under tension to said peripheral edge portions of said leg-openings, said elastic members being stretchable in a leg-surrounding direction; and a pair of substantially liquid-impervious leak-barrier cuffs extending in said leg-surrounding direction in a vicinity of transversely opposite side edges of said liquid-absorbent core, said elastic members comprising:

first and second elastic members extending exclusively in said leg-surrounding direction, with said first elastic members being provided in a front peripheral edge portion of said leg-openings on a side of said front waist region and said second elastic members being provided in a rear peripheral edge portion of the leg-openings on a side of the rear waist region, said first elastic members and said second elastic members being longitudinally spaced apart in a central portion of said crotch region, said leak-barrier cuffs having:

fixed side edge portions extending in said leg-surrounding direction in a vicinity of side edge portions of said liquid-absorbent core;

free side edge portions being contiguous to said fixed side edge portions and normally biased to rise on said liquid-pervious top sheet; and fixed longitudinally opposite end portions collapsed inwardly of said diaper and placed upon said liquid-pervious topsheet in said front and rear waist regions, said free side edge portions of said leak-barrier cuffs extending inward beyond the side edges of said liquid-absorbent core in said crotch region and are folded back along substantially middle folding lines thereof outward beyond the side edges of said liquid-absorbent core, said free side edge portions of said leak-barrier cuffs are bonded, in the vicinity of said middle folding lines, to an outer surface of said liquid-pervious top sheet in an upper zone of the liquid-absorbent core.

4. The disposable pull-on diaper according to claim 3, wherein said first elastic members have a stretch strength higher than a stretch strength of said second elastic members.

\* \* \* \* \*